(12) United States Patent
Hammer

(10) Patent No.: US 9,179,941 B2
(45) Date of Patent: Nov. 10, 2015

(54) SURGICAL CROSS CONNECTOR

(71) Applicant: BLACKSTONE MEDICAL, INC., Lewisville, TX (US)

(72) Inventor: Michael Hammer, Pine Brook, NJ (US)

(73) Assignee: BLACKSTONE MEDICAL, INC., Lewisville, TX (US)

(*) Notice: Subject to any disclaimer, the term of this patent is extended or adjusted under 35 U.S.C. 154(b) by 96 days.

(21) Appl. No.: 13/826,040

(22) Filed: Mar. 14, 2013

(65) Prior Publication Data
US 2014/0277156 A1    Sep. 18, 2014

(51) Int. Cl.
*A61B 17/70*    (2006.01)

(52) U.S. Cl.
CPC .......... *A61B 17/7052* (2013.01); *A61B 17/7007* (2013.01); *A61B 17/7013* (2013.01)

(58) Field of Classification Search
CPC ............. A61B 17/705; A61B 17/7052; A61B 17/7019; A61B 17/7043; A61B 17/7049; A61B 17/7014; A61B 17/7023; A61B 17/7025
USPC .................................. 606/324, 277, 250–253
See application file for complete search history.

(56) References Cited

U.S. PATENT DOCUMENTS

| | | |
|---|---|---|
| 6,238,396 B1 | 5/2001 | Lombardo |
| 6,264,658 B1 * | 7/2001 | Lee et al. ................. 606/254 |
| 7,717,939 B2 | 5/2010 | Ludwig et al. |
| 8,361,117 B2 | 1/2013 | Michielli et al. |
| 2003/0045874 A1 * | 3/2003 | Thomas, Jr. ............... 606/61 |
| 2003/0114853 A1 | 6/2003 | Burgess et al. |
| 2005/0228377 A1 | 10/2005 | Chao et al. |
| 2006/0064091 A1 | 3/2006 | Ludwig et al. |
| 2006/0229616 A1 * | 10/2006 | Albert et al. ............... 606/61 |
| 2010/0160981 A1 | 6/2010 | Butler et al. |
| 2010/0191289 A1 | 7/2010 | Ludwig et al. |
| 2011/0046675 A1 * | 2/2011 | Barrus et al. ............ 606/252 |
| 2011/0307012 A1 | 12/2011 | Mir et al. |
| 2012/0259369 A1 | 10/2012 | Hammer |

FOREIGN PATENT DOCUMENTS

| | | |
|---|---|---|
| WO | 2007040824 A2 | 4/2007 |
| WO | 2010075442 A1 | 7/2010 |

OTHER PUBLICATIONS

International Search Report and Written Opinion, PCT/US2014/024737, dated Jul. 21, 2014, 10 pages.

* cited by examiner

*Primary Examiner* — Eduardo C Robert
*Assistant Examiner* — Julianna N Harvey
(74) *Attorney, Agent, or Firm* — Baker & McKenzie LLP

(57) ABSTRACT

Example embodiments relate generally to an apparatus operable to couple a pair of implantation rods that are surgically implanted adjacent to a plurality of vertebrae. Each implantation rod is secured by at least one fastener element having a head. The apparatus comprises at least one main assembly, said main assembly operable to move relative to a head of one of the fastener elements when not in a locked position. The apparatus also comprises a center link extending in an axial direction, said center link operable to move relative to the main assembly when not in a locked position. The main assembly is operable to receive the center link and a head of one of the fastener elements and secure the center link and the head relative to the main assembly when in a locked position.

31 Claims, 8 Drawing Sheets

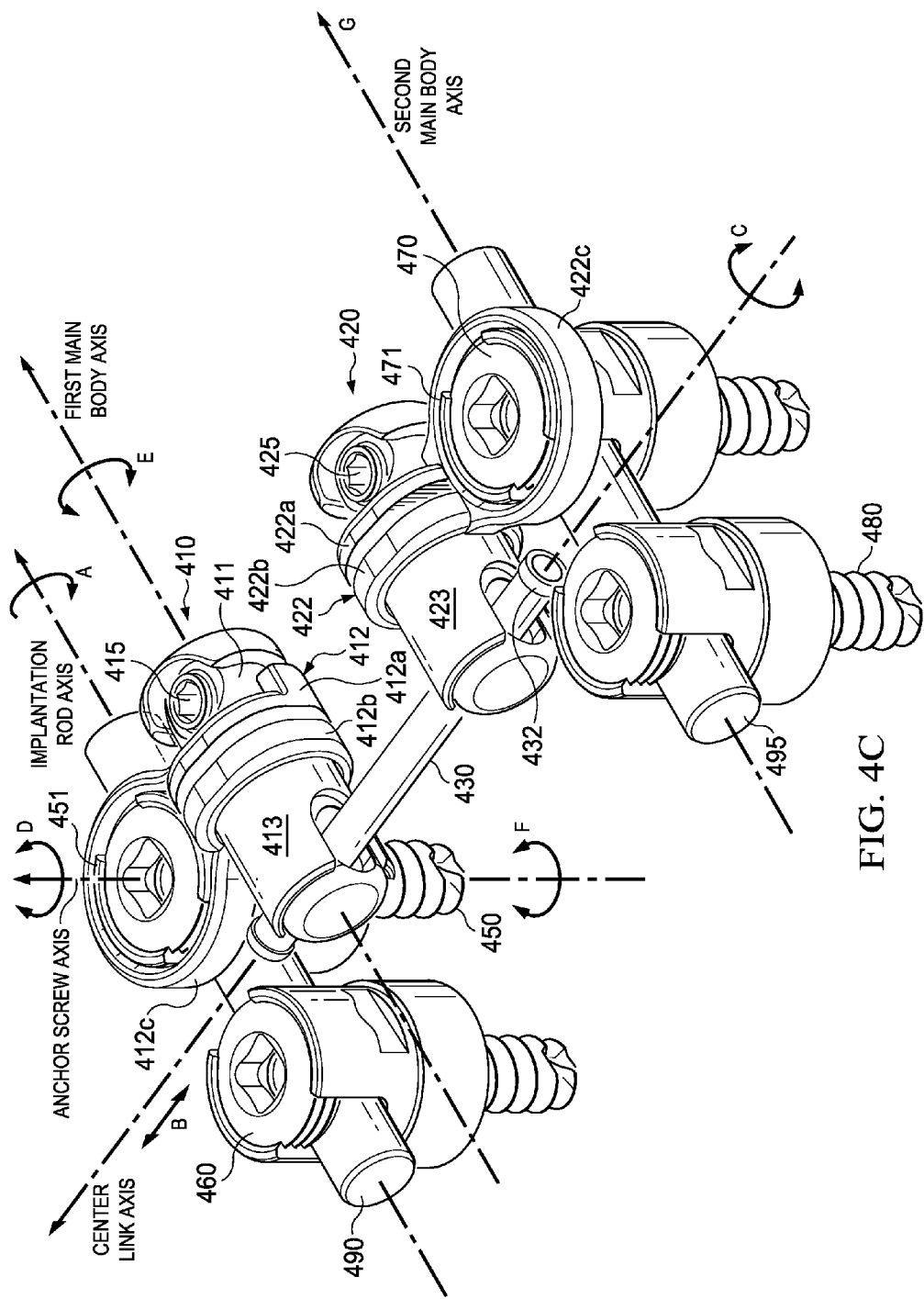

SURGICAL CROSS CONNECTOR

TECHNICAL FIELD

The present disclosure relates generally to a surgical cross connecting apparatus for use with implantation rods.

BACKGROUND

The spinal column is a highly complex interconnection of individual bones coupled together to provide, among other things, protection of the nervous system, while also enabling collective movements in a plurality of directions.

Due to various genetic and/or developmental occurrences, including diseases, developmental irregularities, trauma, stress, and the like, the spinal column may require surgical intervention. To protect and/or aid in the recovery of a surgically repaired section of the spinal column, there are often situations wherein it is desirable to collectively restrict movement of one or more bones of the spinal column.

Immobilization of a section of the spinal column may be achieved using a variety of known surgically implanted support systems and methods, such as use of posterior surgical implants comprising one or more implantation rods. In general, a surgically-implanted rod is fixedly attached by first threading one or more anchor screws to a pedicle of one or more vertebrae of the spinal column. Each anchor screw is in turn fixedly coupled to the implantation rod at proximate locations along its shaft.

In certain patients, it may be desirable to increase the support and torsional rigidity of the surgically-implanted implantation rod system. These situations may require not only support on the side of the spinal column that is attached to an implantation rod, but also torsional rigidity and support collectively between the implantation rods. To achieve this, patients have been selectively provided with surgically implanted cross connector systems to couple between two implantation rods.

SUMMARY

Conventional screw head-type cross connector systems, such as those that secure two implantation rods by attaching to the head of anchor screws (see U.S. Pat. No. 7,717,939), and hook set-type cross connector systems, such as those that secure two implantation rods by attaching hooks to the shaft of the rod (see U.S. Pat. No. 6,238,396), may be employed to couple two implanted rods in situations wherein the implantation rods are substantially parallel relative to each other in every axis (hereinafter "three dimensionally parallel" or "3D parallel") and have a sufficient separation distance between each other. An example of a pair of implantation rods that are three dimensionally parallel is shown in FIG. 1, wherein d represents a minimum separation distance between a first implantation rod (100) and a second implantation rod (200) so as to enable a conventional cross connector system to attach between the two implantation rods.

Due to their limited adjustability, including providing limited screw head to screw head length adjustments, conventional screw head-type cross connector systems are generally not suitable for situations where the implantation rods are not three dimensionally parallel and/or there is insufficient separation distance between screw heads (hereinafter "non-ideal situations" or "non-ideal positions"). An example of two implantation rods (100, 200) that are not three-dimensionally parallel is shown in FIG. 2. Conventional hook set-type cross connector systems have been recently introduced to provide a certain degree of freedom to accommodate more non-ideal situations, particularly those where conventional screw head-type cross connector systems cannot be employed. However, they too have limitations in use, particularly in those situations requiring more degrees of freedom to cross connect in non-ideal situations and/or having insufficient separation distance between screw heads.

In general, non-ideal situations frequently occur in patients requiring increased support and torsional rigidity between sets of bones supported by implantation rods. Because conventional cross connector systems are best suited for attaching in substantially ideal situations and certain limited non-ideal situations, as described earlier, surgeons are more often than not faced with having to perform complicated surgical re-adjustments of the already-implanted implantation rod systems to accommodate the attaching of conventional cross connectors. Surgical re-adjustments may include removing hooks, anchor screws, coupling components, and/or implantation rods, and re-threading the anchor screws and/or re-installing the components in a different location/position/orientation, so as to enable the implantation rods to be substantially three-dimensionally parallel and/or having sufficient separation distance between the screw heads.

In practice, surgeons are often faced with practical problems and difficulties in implanting implantation rods in patients to be substantially three-dimensionally parallel and having sufficient separation distance due to, among other things, the anatomically varying sizes/shapes/orientations of the spinal column and/or the varying degrees and/or nature of surgical repairs required and/or rendered to the spinal column of each particular patient. More often than not, surgeons have little choice other than to implant implantation rods in non-ideal positions relative to each other. This in turn makes it difficult to properly couple conventional cross-connecting systems to such implanted implantation rods, and surgeons are often required to perform complicated surgical re-adjustments of the implanted rods and/or anchor screws to accommodate the conventional cross connector. In general, a tremendous amount of time, planning, effort, precision, and costs are incurred since these tasks typically involve, among other things, surgically removing one or more anchor screws, coupling components, and/or implantation rods, and surgically re-installing them in such a way as to properly accommodate a substantially ideal position of the implantation rods, as required by conventional cross connecting systems.

In considering the above problems, it is recognized herein that providing increased support and torsional rigidity between implantation rods that are implanted in non-ideal positions can be achieved without the need to perform surgical re-adjustments of the implanted implantation rods, coupling components, and/or anchor screws.

Present example embodiments relate generally to an apparatus operable to couple a pair of implantation rods. Each implantation rod is secured by at least two fastener elements having a head. The apparatus comprises at least one main assembly, said main assembly operable to move relative to a head of one of the fastener elements when not in a locked position. The apparatus also comprises a center link extending in an axial direction, said center link operable to move relative to the main assembly when not in a locked position. The main assembly is operable to receive the center link and a head of one of the fastener elements and secure the center link and the head relative to the main assembly when in a locked position.

In accordance with another example embodiment, an apparatus is operable to fixably couple a pair of implantation rods, wherein each implantation rod is secured by at least two fastener elements. The apparatus comprises a center link extending in an axial direction and two or more main assemblies. Each main assembly is operable to receive the center link and a head of one of the fastener elements when not in a locked position. Each main assembly comprises a main body, a center link clamp having an adjustable bore and housed within the main body, an outer sleeve surrounding at least a portion of the main body, an anchor clamp having an adjustable portion and proximate to the main body and the outer sleeve, and an adjustment member operable in cooperation with the main body to adjust the adjustable bore and the adjustable portion. The center link is received in the adjustable bore of the center link clamp and the head is received in the adjustable portion of the anchor clamp. The center link and the head are securable relative to the main body when the adjustment member is actuated into a locked position. Furthermore, the center link is movable relative to the main body and the adjustable portion is movable relative to each main body when the adjustment member is actuated from the locked position.

In another exemplary embodiment, an apparatus is operable to couple an implantation rod to a center link, wherein the implantation rod is secured by at least two fastener elements having a head. The apparatus comprises a main body, a center link clamp having an adjustable bore and housed within the main body, an outer sleeve surrounding at least a portion of the main body, an anchor clamp having an adjustable portion and proximate to the main body and the outer sleeve, and an adjustment member operable in cooperation with the main body to adjust the adjustable bore and the adjustable portion.

BRIEF DESCRIPTION OF THE DRAWINGS

For a more complete understanding of the present disclosure and its advantages, reference is now made to the following description taken in conjunction with the accompanying drawings, in which like reference numbers indicate like features, and:

FIG. 4C is a perspective view of another example embodiment of a cross connector coupled to a pair of implantation rods;

Although similar reference numbers may be used to refer to similar elements for convenience, it can be appreciated that each of the various example embodiments may be considered to be distinct variations.

DETAILED DESCRIPTION

The present invention will now be described hereinafter with reference to the accompanying drawings, which form a part hereof, and which illustrate example embodiments by which the invention may be practiced. As used in the disclosures and the appended claims, the term "example embodiment" does not necessarily refer to a single embodiment, although it may, and various example embodiments may be readily combined and interchanged, without departing from the scope or spirit of the present invention. Furthermore, the terminology as used herein is for the purpose of describing example embodiments only and is not intended to be a limitation of the invention. In this respect, as used herein, the term "in" may include "in" and "on", and the terms "a", "an" and "the" may include singular and plural references. Furthermore, as used herein, the term "by" may also mean "from", depending on the context. Furthermore, as used herein, the term "if" may also mean "when" or "upon", depending on the context. Furthermore, as used herein, the words "and/or" may refer to and encompass any and all possible combinations of one or more of the associated listed items.

Spinal fixation of an implantation rod may be provided by one or more fastener elements, such as an anchor screw, having a head. Typically, one or more anchor screws will be fixedly installed to a pedicle of one or more vertebrae, and correspondingly fixedly coupled about proximate sections of the shaft of the implantation rod. In many situations, a cross connector apparatus may be applied between two implanted implantation rods, particularly when enhanced support and torsional rigidity is required. Hereinafter, an "implanted anchor screw" will refer to an anchor screw that has already been fixedly installed to a vertebra and an "implanted implantation rod" will refer to an implantation rod that has already been fixedly coupled to one or more implanted anchor screws.

Figure 1:
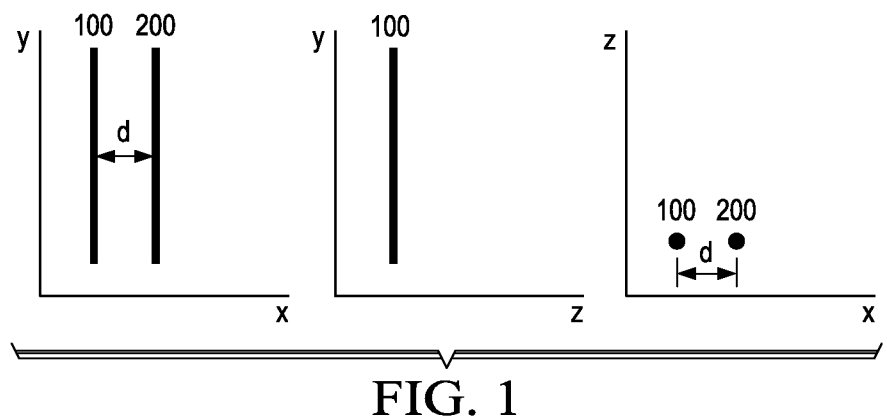
FIG. 1 is an example illustration of a pair of implantation rods that are three-dimensionally parallel.
Figure 2:
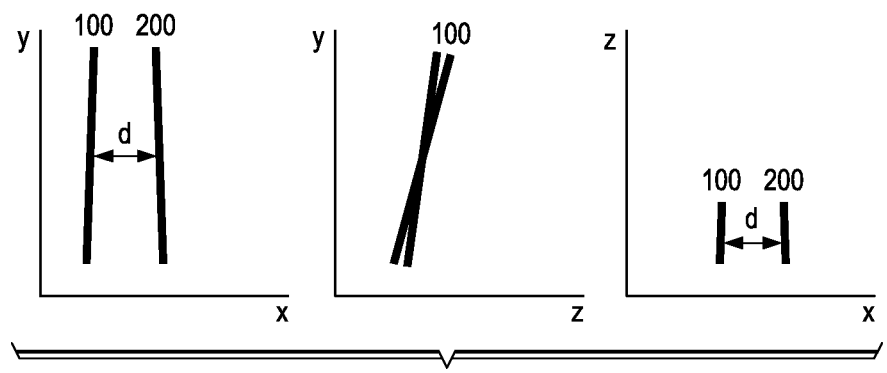
FIG. 2 is an example illustration of a pair of implantation rods that are not three-dimensionally parallel.
Figure 3A:
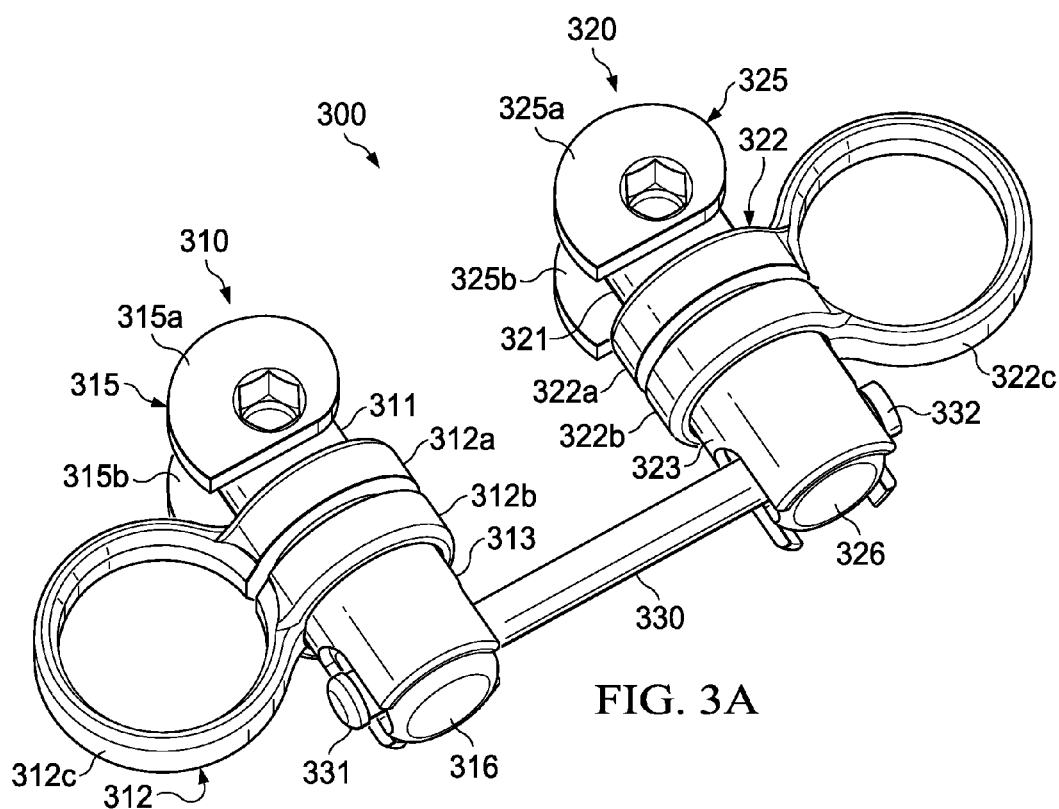
FIG. 3A is a perspective view of an example embodiment of a cross connector.
Figure 3B:
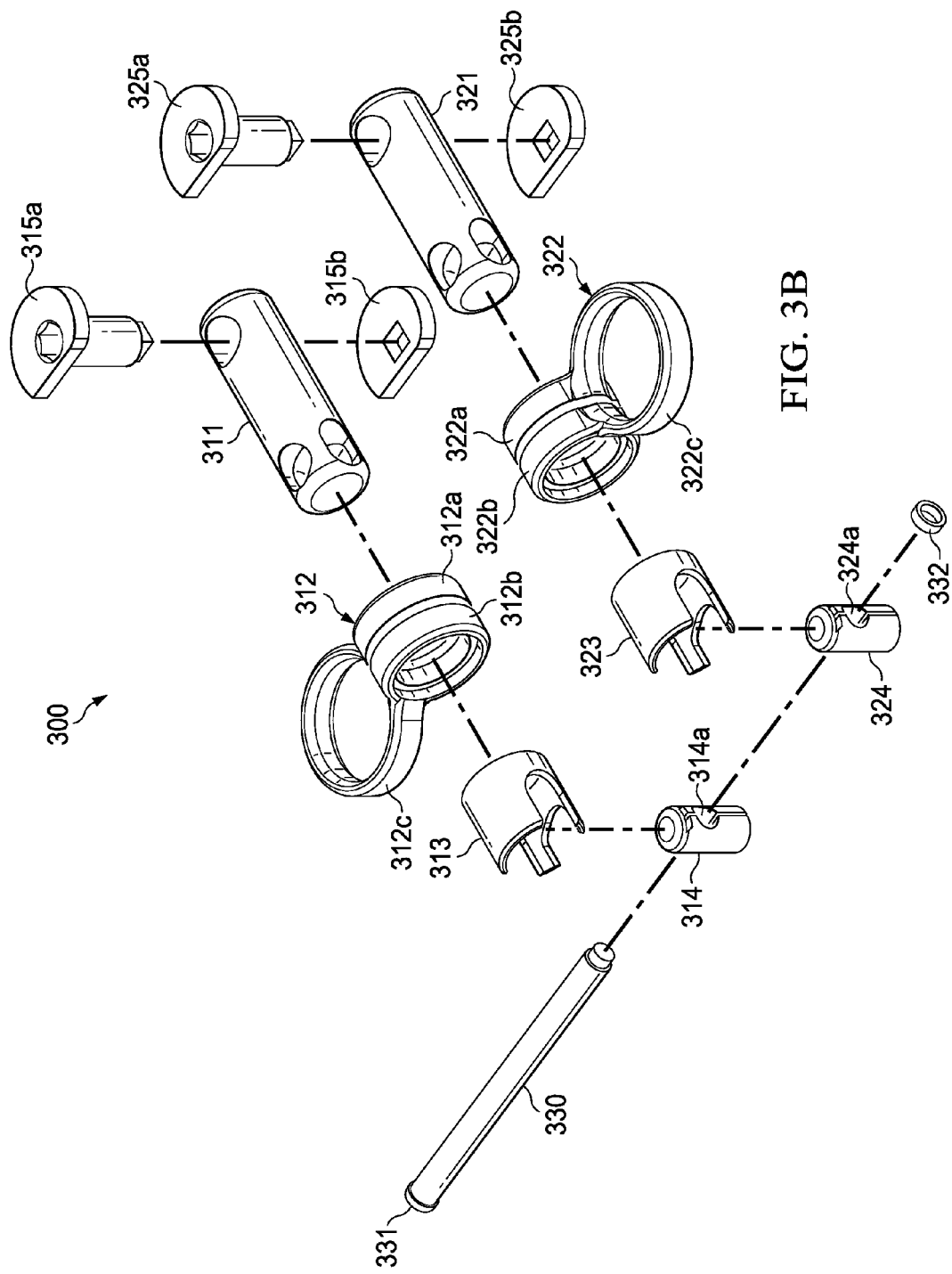
FIG. 3B is an exploded view of an example embodiment of a cross connector.
Figure 3C:
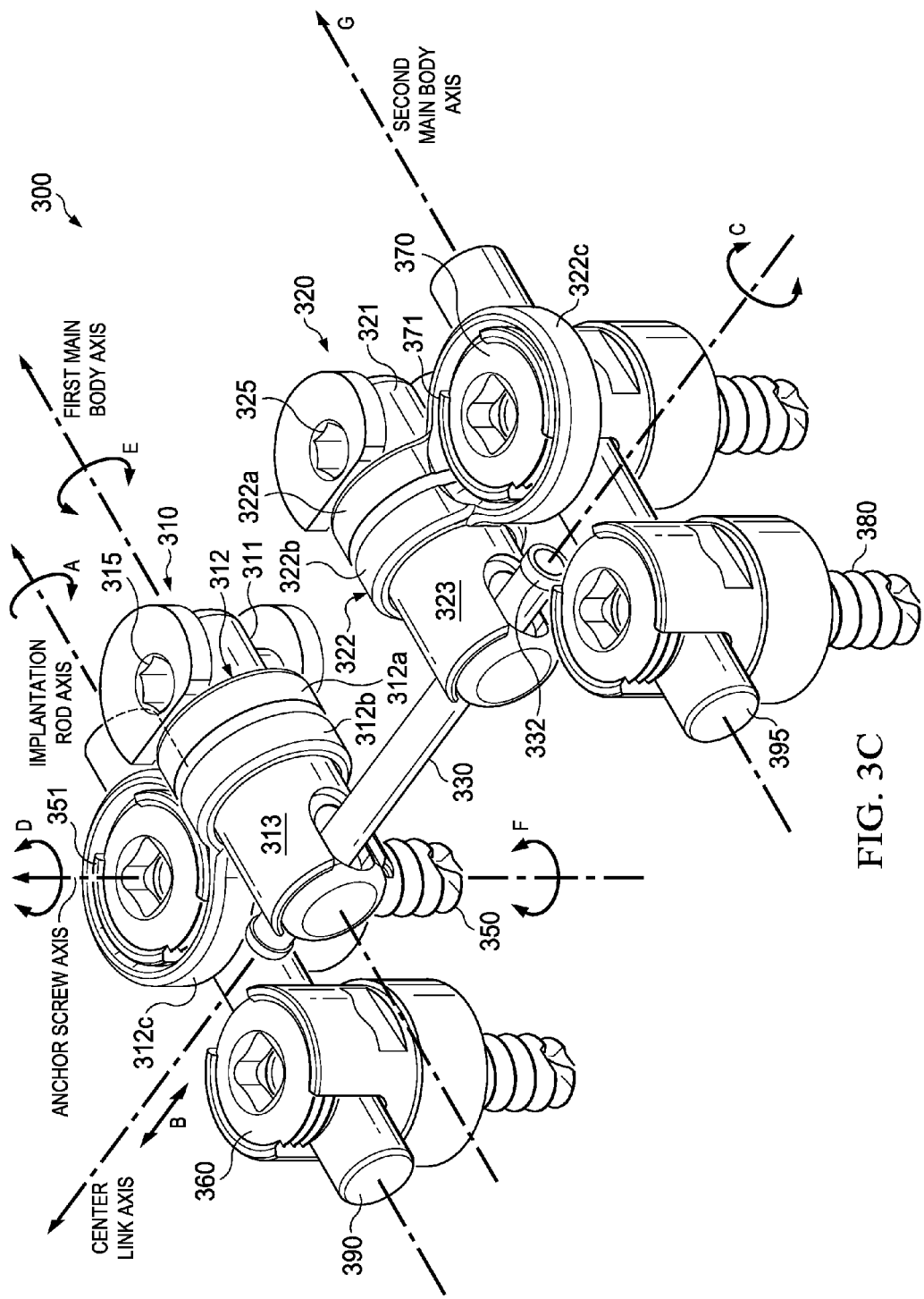
FIG. 3C is a perspective view of an example embodiment of a cross connector coupled to a pair of implantation rods.

Reference is now made to an example embodiment of the cross connector (300) illustrated in FIGS. 3A, 3B and 3C. As shown in FIG. 3A, The cross connector (300) comprises a first main assembly (310), a second main assembly (320), and a center link (330) in communication with the first main assembly (310) and the second main assembly (320). The first main assembly (310) may be substantially the same as, and/or a mirror reflection of, the second main assembly (320), although they may also comprise one or more aspects that are oriented, positioned and/or operated differently so as to accommodate specific implanted anchor screw and implantation rod arrangements. In other words, example embodiments of the cross connector (300) are adaptively adjustable so as to attach in a wide range of non-ideal situations and positions to two or more implanted implantation rods. An example embodiment of the cross connector (300) attached to a set of implanted anchor screws and implantation rods is depicted in FIG. 3C.

Figure 4A:
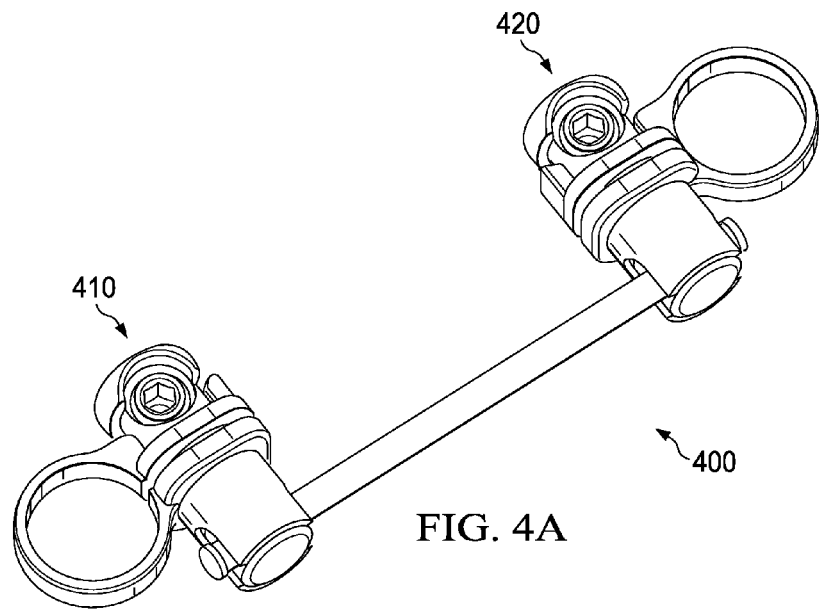
FIG. 4A is a perspective view of another example embodiment of a cross connector.
Figure 4B:
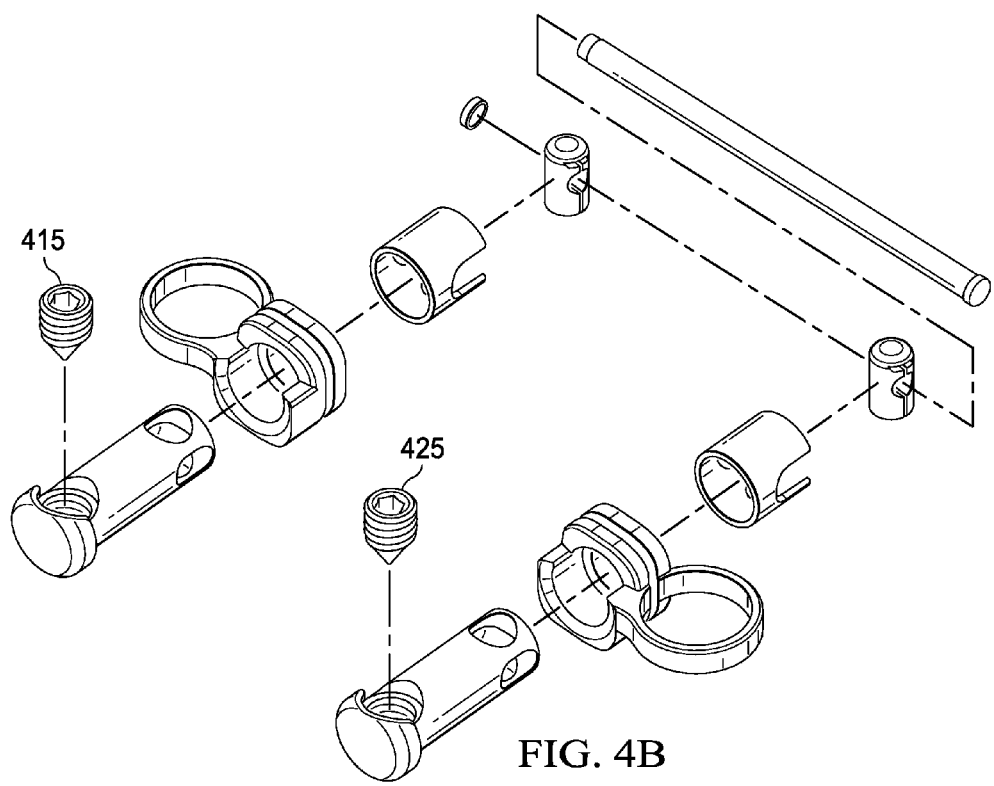
FIG. 4B is an exploded view of another example embodiment of a cross connector.

As shown in FIG. 3B, each of the main assemblies (310, 320) comprise a main body (311, 321), an anchor clamp (312, 322) having a fixably adjustable clamp portion (312c, 322c) for receiving the head (351) of an anchor screw (350), a center link clamp (314, 324) having an adjustable bore (314a, 324a) for receiving the center link (330), an outer sleeve (313, 323) surrounding at least a portion of the main body (311, 321) housing the center link clamp (314, 324), and a set cam assembly (315, 325) comprising a set cam (315a, 325a) and a set cam mating element (315b, 325b) for enabling each main assembly (310, 320) to be brought into and released from a locked position. The center link (330) is preferably an elongated symmetrically-shaped member receivable by the first and second main assemblies (310, 320) in the adjustable bores (314a, 324a) of their respective center link clamps (314, 324), and may include one or more center link nubs (331, 332) to restrict the main assemblies (310, 320) from separating from the center link (330) when not in the locked position. The center link (330) may also take other shapes and forms in other example embodiments, such as elliptical, hexagonal, or other shapes, and may be straight as depicted or curved. It is to be understood by those skilled in the art that actuating to and releasing from a locked position can be achievable in a variety of ways, including the use of a set screw, or the like. An example embodiment of a cross connector (400) being provided with set screws (415, 425) is illustrated in FIGS. 4A, 4B and 4C. Hereinafter, example embodiments of the cross connector will be described with reference to the cross connector (300) having set cams (315, 325) of FIGS. 3A, 3B and 3C, although the descriptions will also be equally applicable to example embodiments of the cross connector (400) that are provided with set screws (415, 425), and the like.

With reference to FIG. 3C, and for the purpose of illustrating exemplary ways in which an example embodiment of the cross connector may be practiced, certain imaginary axes will be hereinafter defined for the first main assembly (310) attached to a certain anchor screw (350) of a certain implantation rod (390). It is to be understood that the following discussion of movements of the first main assembly (310) and center link (330) are also applicable to other applications and situations, such as the first main assembly (310) attaching to any other anchor screw of any other implantation rod that may or may not be in the same orientation as depicted in the drawings, as well as to the second main assembly (320) being attached to any anchor screw of any other implantation rod that may or may not be in the same orientation as depicted in the drawings. Hereinafter, the imaginary axis drawn through the axial center of the anchor screw body (350) will be referred to as the "anchor screw axis" and is labeled as axis D. Furthermore, the imaginary axis drawn through the axial center of the implanted implantation rod (390) will be referred to as the "implantation rod axis" and is labeled as axis A. Furthermore, the imaginary axis drawn through the axial center of the main body (311) will be referred to as the "main body axis" and is labeled as axis E. Furthermore, an imaginary axis drawn through the axial center of the center link (330) will be referred to as the "center link axis" and is labeled as axis C.

When not in the locked position, an example embodiment of the cross connector is provided with a wide degree of freedom of movement about the implantation rod axis A, the anchor screw axis D, the main body axis E, and/or the center link axis C, which enables the cross connector to be adaptively applied between two or more anchor screw heads coupled to implantation rods that may or may not be three-dimensionally parallel and/or may or may not have sufficient separation distance, as required by conventional cross connector systems.

With reference to the axes depicted in FIG. 3C, in an exemplary non-ideal situation, the implanted orientation of one or more implanted anchor screws (350, 360, 370, 380) may be rotated about one or more of the imaginary axes. When not in the locked position, the cross connector (300) is operable to properly receive the head of these anchor screws in one or more ways, depending on the specific implanted orientation of the implanted anchor screws. For example, if the orientation of the implanted anchor screw (350) is rotated relative to the implantation rod axis, as illustrated by uni-directional arrow A, the screw clamp body (312) can be correspondingly rotated about the first main body (311) in a similar manner so as to provide for the plane of the adjustable clamp portion (312c) of the anchor clamp (312) to be substantially parallel to the plane of the face (351) of the anchor screw head (350). Further adjustments, including displacing the first main assembly (310) in either axial direction along the center link (330), as depicted by bi-directional arrow B, rotating the first main assembly (310) about the center link (330), as depicted by axis C, pivoting the center link (330) about the first main body, as depicted by axes E and/or F (see FIGS. 5A and 5B), and/or pivoting the center link (330) about the second main body axis G, can or may need to be affected to properly receive the anchor screw head (351) in the adjustable clamp portion (312c) of the anchor clamp (312). It is to be understood that corresponding adjustments can be readily made in situations wherein the orientation of the implanted anchor screw (350) is rotated in the opposite direction. It is also to be understood that corresponding adjustments can be made to the second body assembly (320) in view of the orientation of the anchor screw (350). It is also to be understood that, in addition to or in replacement of the said possible orientation of the implanted anchor screw (350), corresponding adjustments can or may need to be made to the second main assembly (320) in relation to orientation rotations of the anchor screw (370). These adjustments to the example embodiment of the cross connector (300) can be readily made by persons ordinarily skilled in the art.

In another example, if the orientation of the implanted anchor screw (350) is rotated in either direction relative the center link axis C, the first main assembly (310) can be correspondingly rotated about the center link (330) in a similar manner so as to provide for the plane of the adjustable clamp portion (312c) of the anchor clamp (312) to be substantially parallel to the plane of the face (351) of the anchor screw head (350). Further adjustments, including pivoting the center link (330) about one of the main assemblies (310, 320), as depicted by axes E and/or F (see FIGS. 5A and 5B), transposing the first main assembly (310) in either direction along the center link (330), as depicted by axis B, rotating the first main assembly (310) about the center link axis, as depicted by bi-directional axis C, pivoting the center link (330) about the first main body axis E, and/or pivoting the center link (330) about the second main body axis G, can or may need to be affected to properly receive the anchor screw head (351) in the adjustable clamp portion (312c) of the anchor clamp (312). It is to be understood that corresponding adjustments can be made to the second body assembly (320) in view of the orientation of the anchor screw (350). It is also to be understood that, in addition to or in replacement of the said possible orientation of the implanted anchor screw (350), corresponding adjustments can or may need to be made to the second main assembly (320) in relation to orientation rotations of the anchor screw (370). These adjustments to the example embodiment of the cross connector (300) can be readily made by persons of ordinary skill in the art.

Exemplary adjustments can also be readily made to the orientation and/or position of example embodiments of the cross connector in other non-ideal situations, such as in applications wherein the separation distance between two implanted implantation rods do not allow for the previously-described configurations of having the first and second main assemblies to be applied between the two implanted implantation rods. For example, the cross connector (300) may be operable so as to position one of the main assemblies (310, 320) on opposite sides of an implanted implantation rod (390, 395) while still being in communication with the other main assembly through the center link (330). In example embodiments, both of the main assemblies (310, 320) may be positioned on opposite sides of the two implantation rods (390, 395) while still being in communication with each other through the center link (330). In performing either of these adjustments, the cross connector (300) is adaptably adjustable to accommodate situations where the separation distance between two implanted implantation rods (390, 395) would not enable the previously described configurations, as well as conventional cross connectors, to be applied. These adjustments may also be applied along with other adjustments, such as the previously described adjustments, to properly couple implanted anchor screw(s) (350, 370) that are implanted in non-ideal positions.

After an example embodiment of the cross connector (300) is adjusted so as to allow the adjustable clamp portions (312c) of each of the first anchor clamp (312) and second anchor clamp (322) to properly receive the anchor screw heads (351, 371) of the anchor screws (350, 370) coupled to the implantation rods (390, 395), the cross connector (300) can be fixedly coupled to the implantation rods (390, 395) by actuating both the first and second main assemblies (310, 320) to the locked position. In an example embodiment of the cross connector (300), each of the main assemblies (310, 320) are actuated to the locked position when their respective set cam assembly (315, 325) is turned to the locked position, which causes certain components of the main assembly (310, 320) to be displaced from their neutral positions. In the same manner, and with reference to FIG. 4B, each of the main assemblies (410, 420) of cross connector (400) are actuated to the locked position when their respective set screw assembly (415, 425) is turned to the locked position, which also causes certain components of the main assembly (410, 420) to be displaced from their neutral position.

Figure 5A:
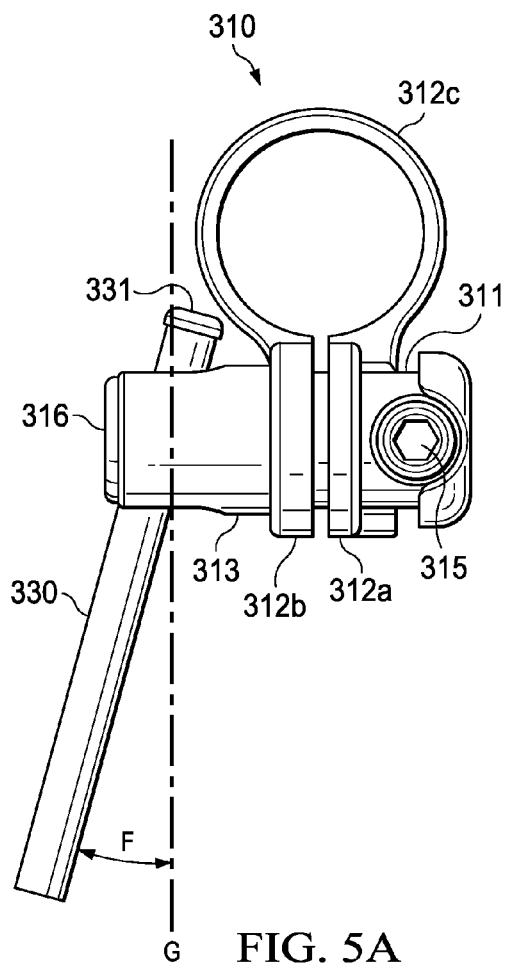
FIG. 5A is a top view of an example embodiment of a cross connector illustrating a pivoting movement of the center link relative to the first and second main assemblies.
Figure 5B:
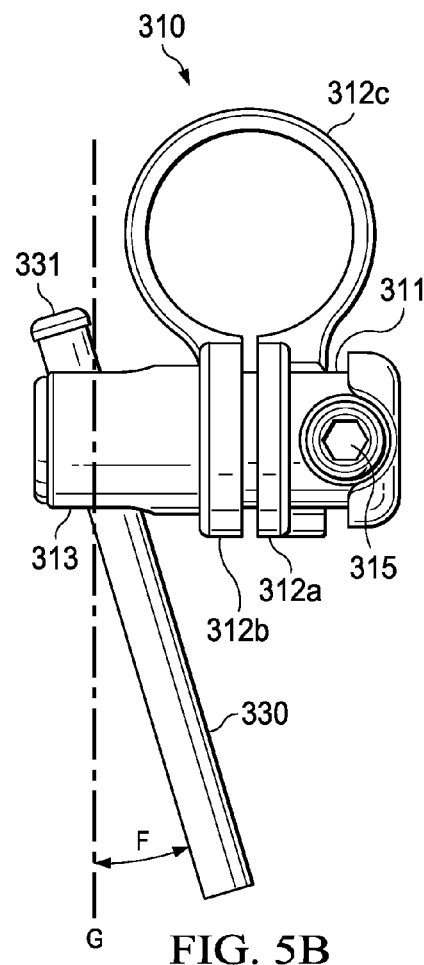
FIG. 5B is a top view of an example embodiment of a cross connector illustrating another pivoting movement of the center link relative to the first and second main assemblies.

FIGS. 5A and 5B are top views of an example embodiment of a cross connector (300) illustrating a pivoting movement of the center link (330) relative to the main assembly (310). In FIG. 5A, the center link (330) can be positioned such that its axis is disposed at an angle +F with respect to the main body axis G. In FIG. 5B, the center link (330) may also be positioned such that its axis is disposed at an angle −F with respect to the main body axis G. This angle F may be in the range of about +20 degrees to about −20 degrees.

Figure 6:
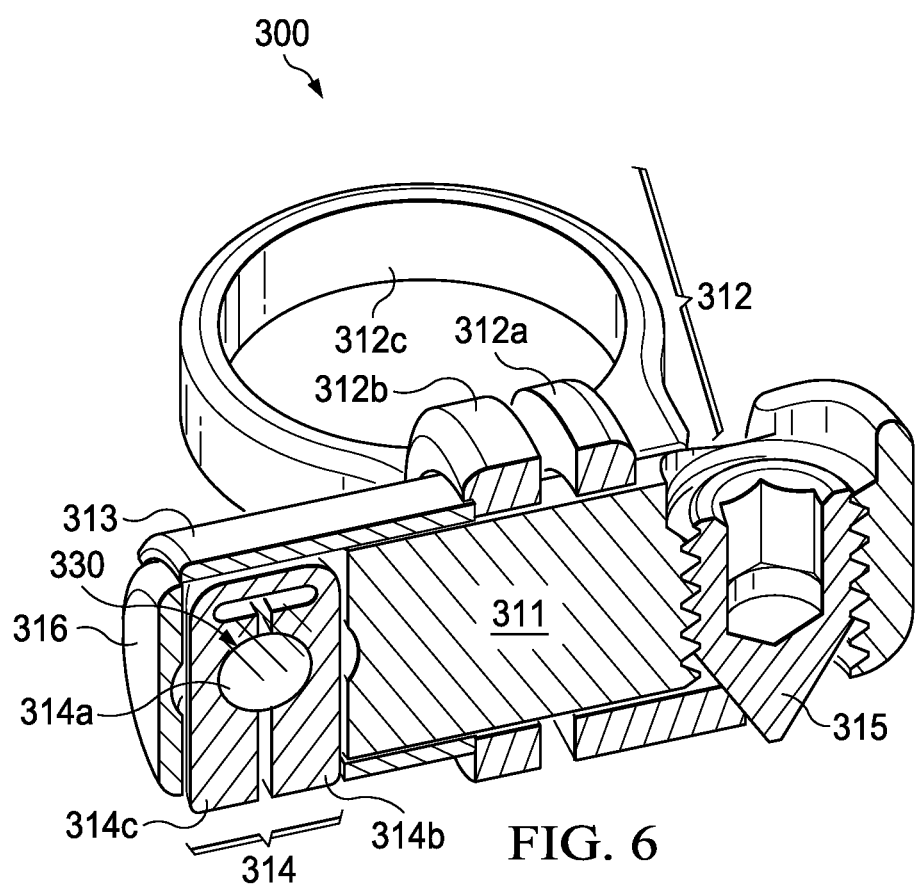
FIG. 6 is a cross sectional view of an example embodiment of a cross connector having a set screw.

In FIG. 6, a cross-sectional illustration of an example embodiment of the cross connector (300) is depicted. When the set screw (315) in FIG. 6 is turned to the locked position, the cylindrical body portions (312a, 312b) of the anchor clamp (312) are driven towards each other. This applies compression to the anchor clamp (312c) that is mounted to the head of a screw. As the set screw (315) is driven into the locked position, a compressive force is also applied to the sides (314b, 314c) of the center link clamp (314) that form the adjustable bore (314a). This causes the center link clamp (314) to compress the diameter of the adjustable bore (314a), thus locking the center link (330) within the main body (300). Effectively, the openings of both the adjustable clamp portion (312c) of the anchor clamp (312) and the adjustable bore (314a) of the center link clamp (314) become adjustably sized as the set screw (315) is driven so as to securely hold the anchor screw head (351) and the center link (330) with respect to the main body, respectively.

While various embodiments in accordance with the disclosed principles have been described above, it should be understood that they have been presented by way of example only, and are not limiting. Thus, the breadth and scope of the invention(s) should not be limited by any of the above-described exemplary embodiments, but should be defined only in accordance with the claims and their equivalents issuing from this disclosure. Furthermore, the above advantages and features are provided in described embodiments, but shall not limit the application of such issued claims to processes and structures accomplishing any or all of the above advantages.

Additionally, the section headings herein are provided for consistency with the suggestions under 37 C.F.R. 1.77 or otherwise to provide organizational cues. These headings shall not limit or characterize the invention(s) set out in any claims that may issue from this disclosure. Specifically, a description of a technology in the "Background" is not to be construed as an admission that technology is prior art to any invention(s) in this disclosure. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings herein.

What is claimed is:

1. An apparatus operable to couple a pair of implantation rods, wherein each implantation rod is secured by at least two fastener elements having a head, the apparatus comprising:
    at least one main assembly operable to move relative to a head of one of the fastener elements when not in a locked position, the main assembly including
        a main body, and
        a center link clamp having an adjustable bore and housed within the main body; and
    a center link extending in an axial direction, the center link operable to move relative to the main assembly when not in a locked position;
    wherein the main assembly is operable to receive the center link and a head of one of the fastener elements;
    wherein the main assembly is operable to secure the center link and the head relative to the main assembly when in a locked position;
    wherein the adjustable bore is a throughhole defined in the center link clamp; and
    wherein a portion of the center link clamp including the throughole is disposed inside the main body.

2. The apparatus of claim 1, wherein the main assembly comprises an outer sleeve surrounding at least a portion of the main body, an anchor clamp having an adjustable portion and proximate to the main body and the outer sleeve, and an adjustment member operable in cooperation with the main body to adjust the adjustable bore and the adjustable portion.

3. The apparatus of claim 2, wherein the center link is received by the adjustable bore of the center link clamp and the head is received by the adjustable portion of the anchor clamp.

4. The apparatus of claim 2, wherein the center link is secured relative to the main body when the adjustment member is actuated into a locked position.

5. The apparatus of claim 4, wherein the adjustment member is a set cam assembly and wherein the set cam assembly secures the center link when a wall of the adjustable bore is contacted against the center link.

6. The apparatus of claim 4, wherein the adjustment member is a set screw and wherein the set screw secures the center link when a wall of the adjustable bore is contacted against the center link.

7. The apparatus of claim 2, wherein the head is secured relative to the main body when the adjustment member is actuated into a locked position.

8. The apparatus of claim 7, wherein the adjustment member is a set cam assembly and wherein the set cam assembly secures the head when a wall of the adjustable portion is contacted against the head.

9. The apparatus of claim 7, wherein the adjustment member is a set screw and wherein the set screw secures the head when a wall of the adjustable portion is contacted against the head.

10. The apparatus of claim 2, wherein the center link is movable relative to the main body when the adjustment member is actuated from a locked position.

11. The apparatus of claim 10, wherein the adjustment member is a set cam assembly and wherein the center link is movable when a wall of the bore is released by the set cam assembly from contacting the center link.

12. The apparatus of claim 10, wherein the adjustment member is a set screw and wherein the center link is movable when a wall of the bore is released by the set screw from contacting the center link.

13. The apparatus of claim 2, wherein the main body is movable relative to the head when the adjustment member is actuated from a locked position.

14. The apparatus of claim 13, wherein the adjustment member is a set cam assembly and wherein the main body is movable relative to the head when a wall of the set cam assembly is released from contacting the anchor clamp.

15. The apparatus of claim 13, wherein the adjustment member is a set screw and wherein the main body is movable relative to the head when a wall of the set screw is released from contacting the anchor clamp.

16. The apparatus of claim 2, wherein the center link clamp is disposed in the outer sleeve.

17. The apparatus of claim 2, wherein the outer sleeve is distinct from the main body.

18. The apparatus of claim 2, wherein the outer sleeve is separable from the main body.

19. The apparatus of claim 1, wherein the center link clamp is distinct from the main body.

20. The apparatus of claim 1, wherein the center link clamp is separable from the main body.

21. The apparatus of claim 1, wherein the center link is operable to be inserted into the throughhole.

22. An apparatus operable to fixably couple a pair of implantation rods, wherein each implantation rod is secured by at least two fastener elements, the apparatus comprising:
a center link extending in an axial direction;
two or more main assemblies, wherein each main assembly is operable to receive the center link and a head of one of the fastener elements when not in a locked position, each main assembly comprising:
a main body;
a center link clamp having an adjustable bore and housed within the main body;
an outer sleeve surrounding at least a portion of the main body;
an anchor clamp having an adjustable portion and proximate to the main body and the outer sleeve; and
an adjustment member operable in cooperation with the main body to adjust the adjustable bore and the adjustable portion;
wherein the center link is received in the adjustable bore of the center link clamp;
wherein the head is received in the adjustable portion of the anchor clamp;
wherein the center link and the head are securable relative to the main body when the adjustment member is actuated into a locked position;
wherein the center link is movable relative to the main body and the adjustable portion is movable relative to each main body when the adjustment member is actuated from the locked position;
wherein the adjustable bore is a throughhole defined in the center link clamp; and
wherein a portion of the center link clamp including the throughole is disposed inside the main body.

23. The apparatus of claim 22, wherein the adjustable member is a set cam assembly and wherein the set cam assembly secures the center link when a wall of the adjustable bore is contacted against the center link and secures the head when a wall of the adjustable portion is contacted against the head.

24. The apparatus of claim 22, wherein the adjustable member is a set screw and wherein the set screw secures the center link when a wall of the adjustable bore is contacted against the center link and secures the head when a wall of the adjustable portion is contacted against the head.

25. An apparatus operable to couple an implantation rod to a center link, wherein the implantation rod is secured by at least two fastener elements having a head, the apparatus comprising:
a main body;
a center link clamp having an adjustable bore and housed within the main body;
an outer sleeve surrounding at least a portion of the main body;
an anchor clamp having an adjustable portion and proximate to the main body and the outer sleeve; and
an adjustment member operable in cooperation with the main body to adjust the adjustable bore and the adjustable portion;
wherein the adjustable bore is a throughhole defined in the center link clamp; and
wherein a portion of the center link clamp including the throughole is disposed inside the main body.

26. The apparatus of claim 25, wherein the center link is received by the adjustable bore of the center link clamp and the head is received by the adjustable portion of the anchor clamp.

27. The apparatus of claim 25, wherein the center link is securable relative to the main body when the adjustment member is actuated into a locked position.

28. The apparatus of claim 25, wherein the head is securable relative to the main body when the adjustment member is actuated into a locked position.

29. The apparatus of claim 25, wherein the center link is movable relative to the main body when the adjustment member is actuated from the locked position.

30. The apparatus of claim 25, wherein the main body is movable relative to the head when the adjustment member is actuated from the locked position.

31. The apparatus of claim 25, wherein the adjustment member is a set cam assembly or a set screw.

* * * * *